(12) United States Patent
Knight et al.

(10) Patent No.: US 11,240,992 B2
(45) Date of Patent: Feb. 8, 2022

(54) RADIO DEVICE FOR IMPLANTATION IN AN ANIMAL

(71) Applicant: Somark Group Limited, Sydney (AU)

(72) Inventors: Adrian Knight, Sydney (AU); Paul Donohoe, Sydney (AU)

(73) Assignee: Somark Group Limited, Sydney (AU)

( * ) Notice: Subject to any disclaimer, the term of this patent is extended or adjusted under 35 U.S.C. 154(b) by 635 days.

(21) Appl. No.: 16/077,729

(22) PCT Filed: Feb. 11, 2017

(86) PCT No.: PCT/AU2017/050117
§ 371 (c)(1),
(2) Date: Aug. 13, 2018

(87) PCT Pub. No.: WO2017/136898
PCT Pub. Date: Aug. 17, 2017

(65) Prior Publication Data
US 2020/0060229 A1    Feb. 27, 2020

Related U.S. Application Data

(60) Provisional application No. 62/294,084, filed on Feb. 11, 2016, provisional application No. 62/308,330, filed on Mar. 15, 2016.

(51) Int. Cl.
*A01K 11/00*    (2006.01)
*G06K 19/07*    (2006.01)
(Continued)

(52) U.S. Cl.
CPC ........ *A01K 11/004* (2013.01); *G06K 19/0723* (2013.01); *G06K 19/07758* (2013.01); *H01Q 1/273* (2013.01); *H01Q 9/285* (2013.01)

(58) Field of Classification Search
CPC .............................. A01K 11/00; A01K 11/004
(Continued)

(56) References Cited

U.S. PATENT DOCUMENTS

| 3,658,061 A | 4/1972 | Hall |
| 4,223,674 A | 9/1980 | Fluent et al. |

(Continued)

FOREIGN PATENT DOCUMENTS

| AU | 2018200814 B2 | 3/2018 |
| AU | 2017218461 A1 | 9/2018 |

(Continued)

OTHER PUBLICATIONS

Brochure, PhenoSys GmbH, "Individual Tracking—Activity Monitor," Techology for Behavior Analysis, date unknown, 1 page.

(Continued)

*Primary Examiner* — Richard T Price, Jr.
(74) *Attorney, Agent, or Firm* — Patterson Thuente Pedersen, P.A.

(57) ABSTRACT

A radio device for implantation in an animal. The radio device comprises a capsule encapsulating at least one of a radio receiver and a radio transmitter. Also disclosed herein is a method for making a radio device for implantation in an animal, a method for providing electrical power to a radio device attached to an animal, and a method for implanting a radio device into an animal.

10 Claims, 10 Drawing Sheets

(51) Int. Cl.
  *G06K 19/077* (2006.01)
  *H01Q 1/27* (2006.01)
  *H01Q 9/28* (2006.01)

(58) Field of Classification Search
  USPC .............................................. 119/655, 650
  See application file for complete search history.

(56) References Cited

U.S. PATENT DOCUMENTS

| | | | |
|---|---|---|---|
| 4,262,632 | A | 4/1981 | Hanton et al. |
| 4,392,493 | A | 7/1983 | Niemeijer |
| 4,440,078 | A | 4/1984 | McCrery, Jr. et al. |
| 4,671,277 | A | 6/1987 | Beuchat |
| 4,950,249 | A | 8/1990 | Jagger et al. |
| 5,024,727 | A | 6/1991 | Campbell et al. |
| 5,053,774 | A | 10/1991 | Schuermann et al. |
| 5,074,318 | A | 12/1991 | Campbell et al. |
| 5,151,089 | A | 9/1992 | Kirk, III et al. |
| 5,211,129 | A | 5/1993 | Taylor et al. |
| 5,232,455 | A | 8/1993 | Hollister |
| 5,250,026 | A | 10/1993 | Ehrlich et al. |
| 5,288,291 | A | 2/1994 | Teoh |
| 5,551,319 | A | 9/1996 | Spaulding et al. |
| 5,632,732 | A | 5/1997 | Szabo et al. |
| 5,673,647 | A | 10/1997 | Pratt |
| 5,709,662 | A | 1/1998 | Olive et al. |
| 5,816,197 | A | 10/1998 | DeStefano et al. |
| D405,882 | S | 2/1999 | Yale |
| 6,013,122 | A | 1/2000 | Klitzman et al. |
| 6,033,421 | A | 3/2000 | Theiss et al. |
| 6,115,636 | A | 9/2000 | Ryan |
| 6,186,144 | B1 | 2/2001 | Davis et al. |
| 6,263,762 | B1 | 7/2001 | Zeitler |
| 6,345,553 | B1 | 2/2002 | Adler et al. |
| 6,616,638 | B2 | 9/2003 | Peters, III |
| 6,695,819 | B2 | 2/2004 | Kobayashi |
| 6,719,737 | B2 | 4/2004 | Kobayashi |
| 6,901,885 | B1 | 6/2005 | Kleinsasser |
| 7,098,394 | B2 | 8/2006 | Armer et al. |
| 7,230,539 | B2 * | 6/2007 | Klein .................. A01K 11/006 |
| | | | 119/863 |
| 7,553,293 | B2 | 6/2009 | Jensen et al. |
| D609,804 | S | 2/2010 | Uchida et al. |
| 8,353,917 | B2 | 1/2013 | Mandecki et al. |
| 8,502,670 | B2 | 8/2013 | Cha et al. |
| 9,418,321 | B1 | 8/2016 | Gruda et al. |
| 10,349,630 | B2 | 7/2019 | Florczak |
| 10,645,905 | B2 | 5/2020 | Gandola et al. |
| D899,594 | S | 10/2020 | Wang |
| D902,402 | S | 11/2020 | Wang |
| 2002/0020646 | A1 | 2/2002 | Groth et al. |
| 2002/0154065 | A1 | 10/2002 | Mejia et al. |
| 2003/0062988 | A1 | 4/2003 | Mandecki et al. |
| 2004/0097780 | A1 | 5/2004 | Otsuka |
| 2004/0131234 | A1 | 7/2004 | Long et al. |
| 2004/0144333 | A1 | 7/2004 | Finlayson |
| 2004/0220527 | A1 | 11/2004 | Buckley et al. |
| 2004/0244341 | A1 | 12/2004 | Kurt |
| 2004/0246126 | A1 | 12/2004 | Pitts |
| 2004/0260270 | A1 | 12/2004 | Cohen |
| 2005/0051109 | A1 | 3/2005 | Fantin et al. |
| 2005/0234475 | A1 | 10/2005 | Cordes et al. |
| 2006/0071782 | A1 | 4/2006 | Ahmed et al. |
| 2006/0071785 | A1 | 4/2006 | Ahmed et al. |
| 2006/0177649 | A1 | 8/2006 | Clark et al. |
| 2007/0103314 | A1 | 5/2007 | Giessler |
| 2007/0272157 | A1 | 11/2007 | Uner et al. |
| 2007/0288249 | A1 | 12/2007 | Rowe et al. |
| 2008/0008357 | A1 | 1/2008 | Barreto Martins |
| 2008/0036356 | A1 | 2/2008 | Ward et al. |
| 2008/0036846 | A1 | 2/2008 | Hopkins et al. |
| 2008/0042849 | A1 | 2/2008 | Saito et al. |
| 2008/0065181 | A1 | 3/2008 | Stevenson |
| 2008/0106419 | A1 | 5/2008 | Sakama et al. |
| 2008/0143619 | A1 | 6/2008 | Wotherspoon |
| 2008/0158432 | A1 | 7/2008 | Hwang et al. |
| 2008/0168948 | A1 | 7/2008 | Truitt et al. |
| 2008/0221549 | A1 | 9/2008 | Cohen |
| 2008/0247637 | A1 | 10/2008 | Gildenberg |
| 2008/0306437 | A1 | 12/2008 | Jacobson et al. |
| 2008/0314325 | A1 | 12/2008 | Hempstead et al. |
| 2009/0062748 | A1 | 3/2009 | Moller et al. |
| 2009/0153304 | A1 | 6/2009 | Sands et al. |
| 2009/0182267 | A1 | 7/2009 | Painchaud et al. |
| 2009/0209903 | A1 | 8/2009 | Cherif-Cheikh et al. |
| 2009/0241857 | A1 * | 10/2009 | Zolfaghari .............. G09F 3/005 |
| | | | 119/858 |
| 2009/0273439 | A1 | 11/2009 | Selsor |
| 2009/0292246 | A1 | 11/2009 | Slate et al. |
| 2009/0311295 | A1 | 12/2009 | Mathiowitz et al. |
| 2010/0023021 | A1 | 1/2010 | Flaherty |
| 2010/0160809 | A1 | 6/2010 | Laurence et al. |
| 2010/0222767 | A1 | 9/2010 | Gluck |
| 2010/0295682 | A1 | 11/2010 | August et al. |
| 2010/0295687 | A1 | 11/2010 | Kuzniar et al. |
| 2011/0077659 | A1 | 3/2011 | Mandecki et al. |
| 2011/0304505 | A1 | 12/2011 | Parker et al. |
| 2011/0316693 | A1 | 12/2011 | Loen |
| 2012/0016315 | A1 | 1/2012 | Radmer et al. |
| 2012/0086620 | A1 | 4/2012 | Johnson |
| 2012/0126948 | A1 | 5/2012 | Brunski |
| 2012/0193415 | A1 | 8/2012 | Coiro, Sr. et al. |
| 2012/0226288 | A1 | 9/2012 | Mays et al. |
| 2013/0267962 | A1 | 10/2013 | Michelson |
| 2014/0055248 | A1 | 2/2014 | Hammelbacher |
| 2014/0128880 | A1 | 5/2014 | Gandola et al. |
| 2014/0204400 | A1 | 7/2014 | Budleski |
| 2015/0004679 | A1 | 1/2015 | Conger et al. |
| 2015/0032060 | A1 | 1/2015 | Patel |
| 2015/0217059 | A1 | 8/2015 | Ashby et al. |
| 2015/0269798 | A1 * | 9/2015 | Small ...................... G07C 9/28 |
| | | | 119/51.02 |
| 2016/0037749 | A1 | 2/2016 | Gandola et al. |
| 2017/0124264 | A1 | 5/2017 | Jordan et al. |
| 2018/0017679 | A1 | 1/2018 | Valouch et al. |
| 2018/0242899 | A1 | 8/2018 | Oddsson et al. |
| 2019/0053465 | A1 | 2/2019 | Knight et al. |
| 2019/0391002 | A1 | 12/2019 | Knih |
| 2020/0045932 | A1 | 2/2020 | Knight et al. |
| 2020/0296926 | A1 | 9/2020 | Nebolan et al. |
| 2020/0404882 | A1 | 12/2020 | Gandola et al. |

FOREIGN PATENT DOCUMENTS

| | | |
|---|---|---|
| CN | 2602591 Y | 2/2004 |
| CN | 1547430 A | 11/2004 |
| CN | 101057561 A | 10/2007 |
| EP | 0300110 A2 | 1/1989 |
| EP | 0 364 044 A1 | 4/1990 |
| EP | 1911347 A1 | 4/2008 |
| EP | 2840890 A1 | 3/2015 |
| EP | 2967000 A1 | 1/2016 |
| EP | 3413704 A1 | 12/2018 |
| EP | 3694595 A1 | 8/2020 |
| GB | 2468587 A | 9/2010 |
| JP | H05-317278 A | 12/1993 |
| JP | 2009-069108 A | 4/2009 |
| JP | 3152587 U | 8/2009 |
| JP | 2009-232786 A | 10/2009 |
| JP | 2010-266289 A | 11/2010 |
| JP | 2013-503641 A | 2/2013 |
| JP | 6376570 B2 | 8/2018 |
| KR | 20090058746 A | 6/2009 |
| KR | 10-1940275 B1 | 1/2019 |
| SG | 11201507292 | 10/2015 |
| SG | 10201707223 | 10/2017 |
| WO | WO 1998/041084 A1 | 9/1998 |
| WO | WO 2002/082892 A2 | 10/2002 |
| WO | WO 2007/033407 A1 | 3/2007 |
| WO | WO 2011/028926 A2 | 3/2011 |
| WO | WO 2013/163339 A1 | 10/2013 |
| WO | WO 2014/151852 A1 | 9/2014 |
| WO | WO 2015/005802 A1 | 1/2015 |
| WO | WO 2016/113554 A1 | 7/2016 |

(56) References Cited

FOREIGN PATENT DOCUMENTS

| WO | WO 2017/093453 A1 | 6/2017 |
|----|-------------------|--------|
| WO | WO 2017/131337 A1 | 8/2017 |
| WO | WO 2017/136898 A1 | 8/2017 |
| WO | WO 2017/136900 A1 | 8/2017 |
| WO | WO 2019/071317 A1 | 4/2019 |
| WO | WO 2019/071320 A1 | 4/2019 |
| WO | WO 2019/071321 A1 | 4/2019 |
| WO | WO 2020/220043 A1 | 10/2020 |

OTHER PUBLICATIONS

Webpage, "Revolyzer: Voluntary Running Assay," preclinics, 1 page.

Brochure, PhenoSys GmbH, "Activity Monitor," Technology for Behavior Analysis, 3 page.

Mainetti, "An RFID-Based Smart Cage for Animal Behavior Analysis," Smart 2014: The Third International Conference on Smart Systems, 2014, 6 pages.

"Mysensalab" available Aug. 29, 2020, [online], [site visited Aug. 29, 2020]. Retrieved from Internet, URL: https://mysensalab.com/products/ (Year: 2020).

PCT/AU2017/050117, Search Report and Written Opinion dated Jun. 13, 2017, 16 pages.

Application and File history for U.S. Appl. No. 29/701,974, filed Aug. 15, 2019. Inventors: Bates et al.

Application and File history for U.S. Appl. No. 16/755,329, filed Apr. 10, 2020. Inventors: Nebolan et al.

Application and File history for U.S. Appl. No. 16/871,491, filed May 11, 2020. Inventors: Gandola et al.

Application and File history for U.S. Appl. No. 14/778,489, filed Sep. 18, 2015. Inventors: Gandola et al.

Application and File history for U.S. Appl. No. 16/077,728, filed Aug. 13, 2018. Inventors: Knight et al.

Application and File history for U.S. Appl. No. 16/077,727, filed Aug. 13, 2018. Inventors: Knight et al.

Application and File history for U.S. Appl. No. 16/077,730, filed Aug. 13, 2018. Inventors: Knight et al.

Application and File history for U.S. Appl. No. 16/755,323, filed Apr. 10, 2020. Inventors: Knight et al.

Application and File history for U.S. Appl. No. 16/755,309, filed Apr. 10, 2020. Inventors: Knight et al.

\* cited by examiner

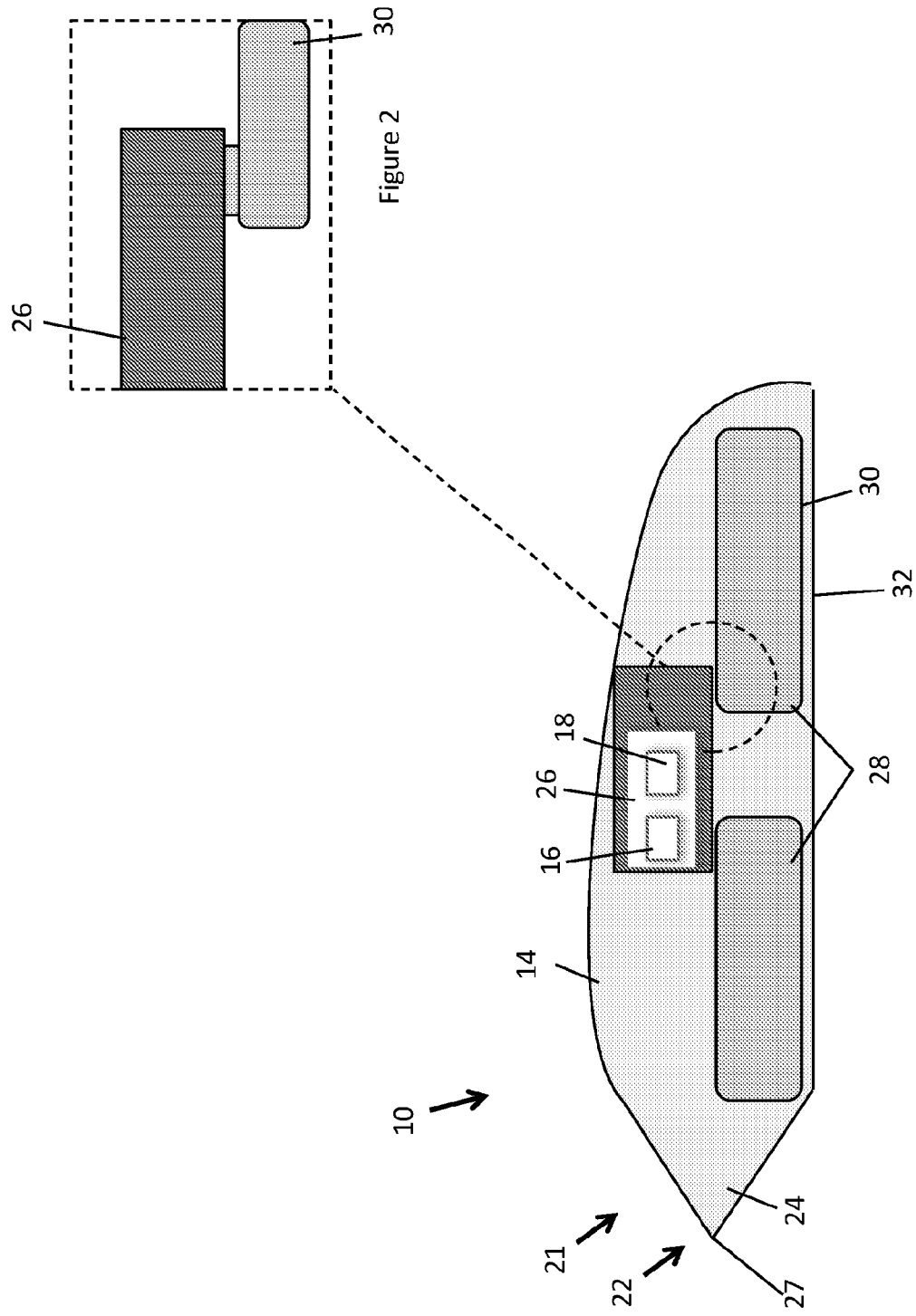

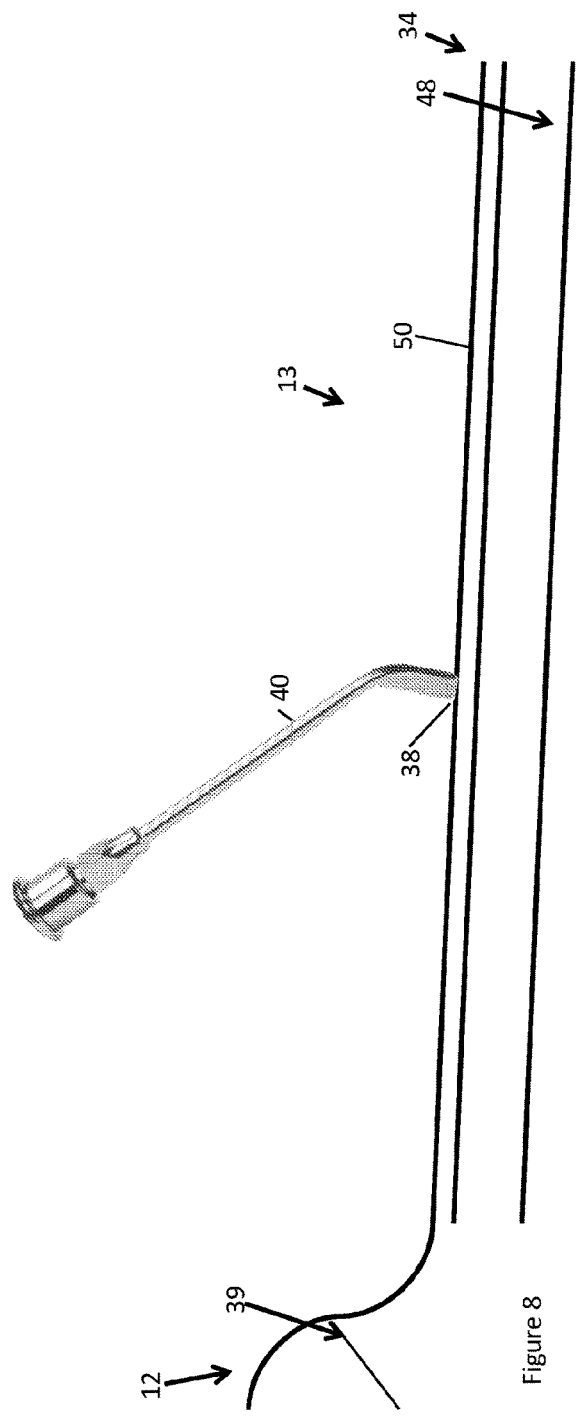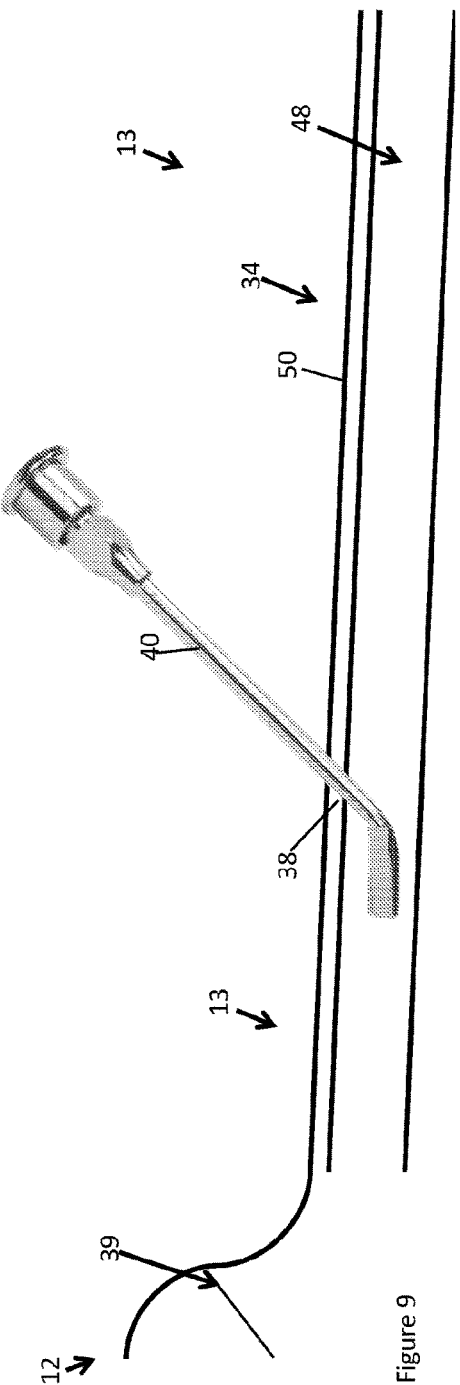

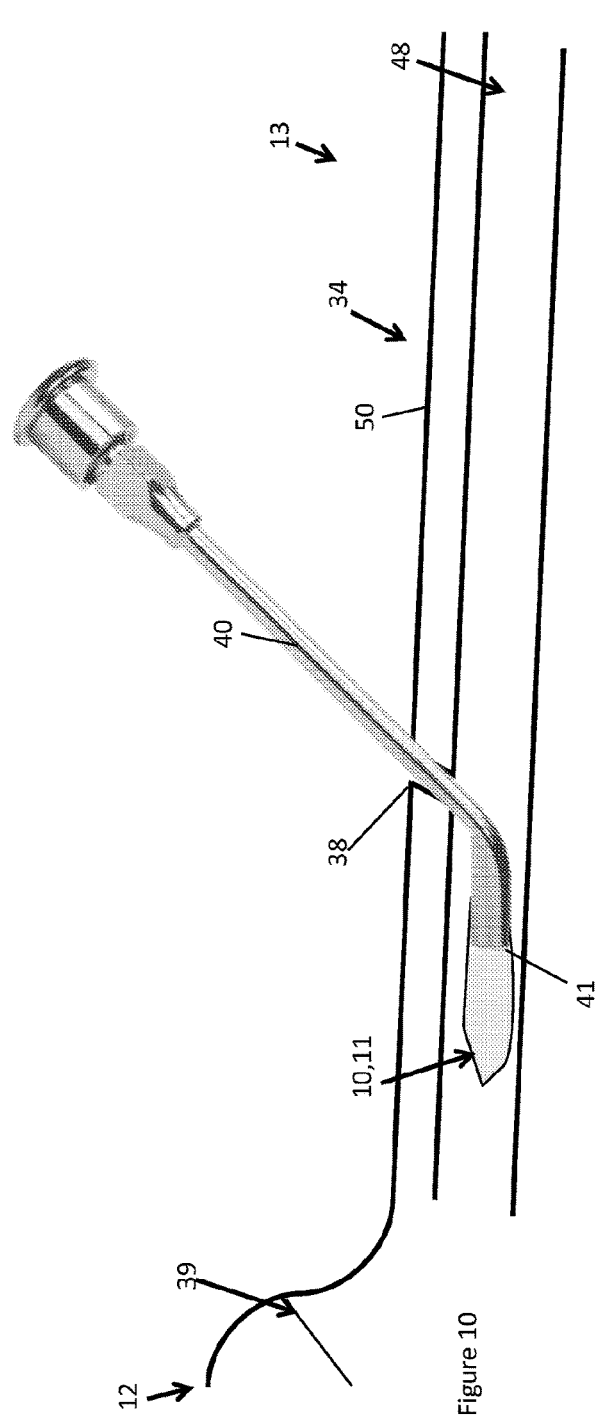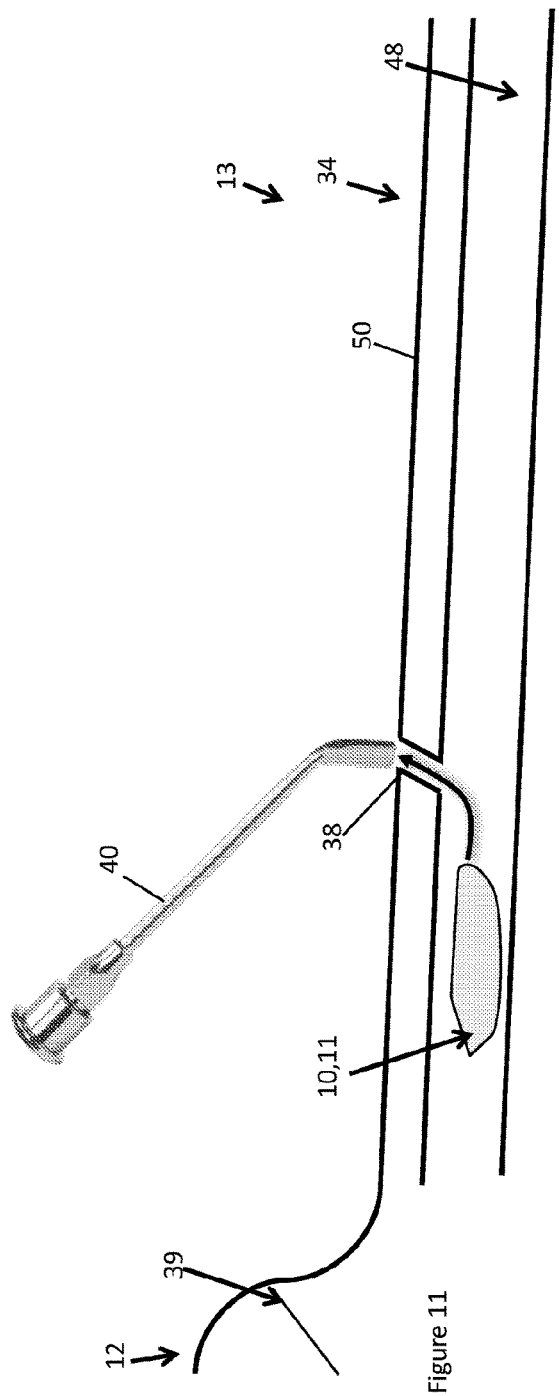

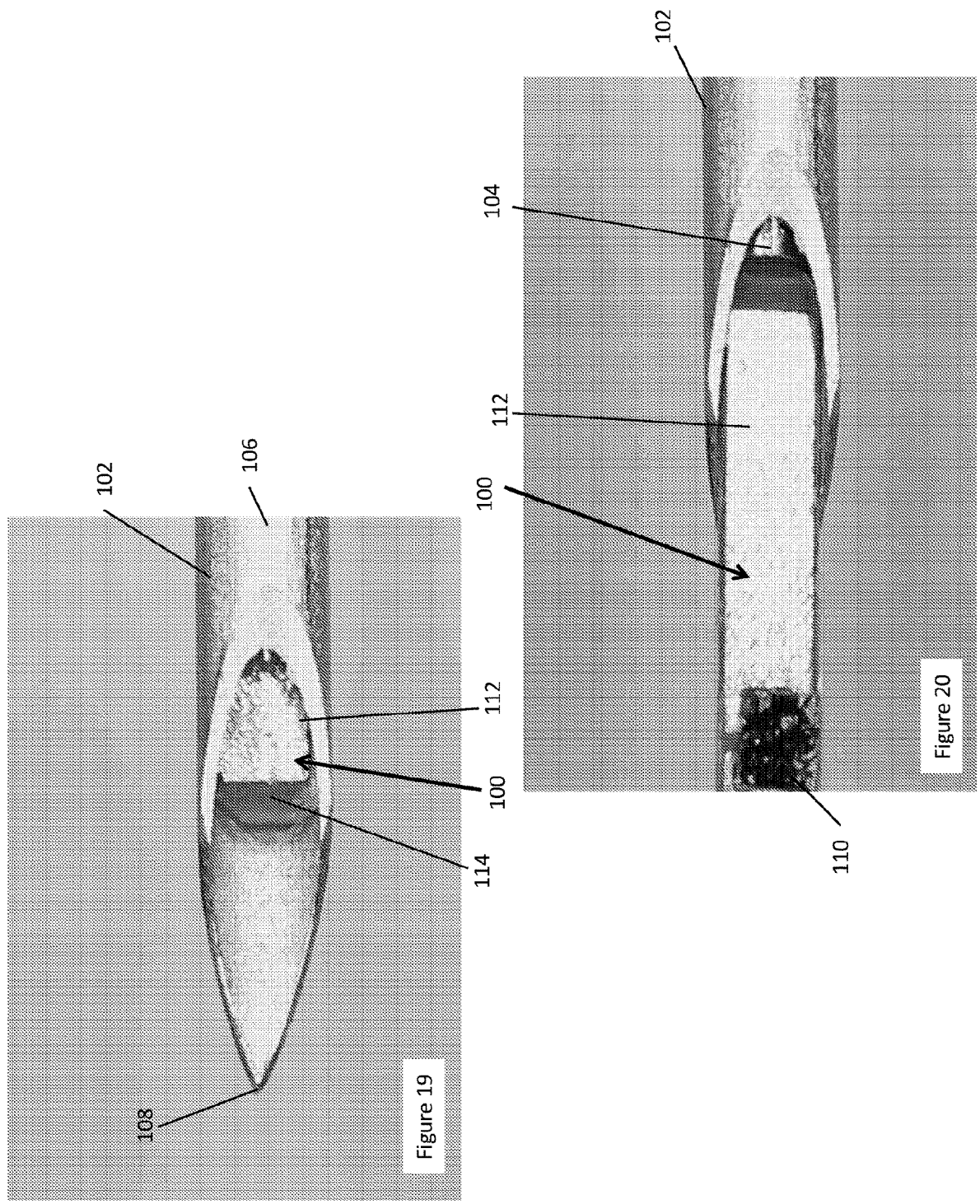

RADIO DEVICE FOR IMPLANTATION IN AN ANIMAL

The present application is a National Phase entry of PCT Application No. PCT/AU2017/050117, filed Feb. 11, 2017, which claims the benefit of U.S. Provisional Patent Application No. 62/294,084, filed Feb. 11, 2016, and U.S. Provisional Application No. 62/308,330, filed Mar. 15, 2016, which are incorporated herein by reference.

TECHNICAL FIELD

The disclosure herein generally relates to a radio device for implantation in an animal, a method for making a radio device for implantation in an animal, a method for providing electrical power to a radio device attached to an animal, a method for implanting a radio device into an animal, an animal having implanted therein a radio device, and a radio device implanted in an animal.

BACKGROUND

Animal husbandry and animal experimentation, meat processing and animal health monitoring, for example, may require identification of an animal, or identification of each of a plurality of animals.

A passive radio-frequency identification (RFID) tag may be used to identify an animal. RFID tags are designed to be small to reduce discomfort to the animal. Passive RFID tags are powered by an externally generated electromagnetic wave in the form of an interrogation radio wave. RFID tags have a radio receiver for receiving the interrogation radio wave and a radio transmitter for transmitting a radio wave comprising identification information in response to the received interrogation radio wave.

The maximum distance that a RFID tag may be read is dependent on the power of the interrogation radio wave and the size of the RFID tag's antenna. The power of the interrogation radio wave may be limited by, for example, regulation or practicalities. While limited interrogation radio wave power may be somewhat compensated by increasing antenna size, the RFID tags used in animal identification, may generally not have sufficiently large antenna because of practical or welfare constraints.

The smallest commercially available RFID tags for animals, to the applicant's knowledge, have a length of 6 mm and a diameter of 1 mm. The size of a RFID tag limits where it can be implanted within an animal. An RFID tag of these dimensions may be disposed between the scapulae ("interscapularly") of a rodent, for example, however may be to large to be disposed elsewhere.

RFID tags may migrate to other locations within the animal even when coated with material for bonding with surrounding tissue, which has been known to compromise the welfare of the animal or cause death. The animal may subsequently require handling to read the migrated RFID tag, which may stress the animal.

In view of their size, RFID tags may cause pain when implanted in an animal. Pain may be relieved with anaesthetic. Anaesthetics, however, may kill animals, cause animal stress, and increase the cost and time associated with an implantation procedure.

The RFID implantation procedure may require manual work by a highly trained and skilled professional. Human error, imprecision and/or misjudgement may result in an inoperable or compromised RFID tag, and stress, damage, or death of the animal. The current implantation devices are generally one time use only, resulting in a significant quantity of sharp waste.

The interrogation radio wave may be degraded and/or attenuated by the vasculature, bones and muscles, for example. Low (e.g. 125-134 KHz) or medium (e.g. 13.2-13.6 MHz) radio frequencies may be used as these may be attenuated and/or degraded less than other frequencies, however even these frequencies may be attenuated and/or degraded.

Current RFID tags for animals may generally operate at low radio frequencies because water, of which animals are significantly composed, attenuates higher radio frequencies that include but are not limited to radio frequencies in the ultra-high frequency (UHF) band (300 MHz-3 GHz).

Low radio frequency tags may be more expensive to manufacture than is generally desirable. Low radio frequency RFID tags may have a coil for an antenna, which for 125 KHz radio frequencies may have over a hundred turns to produce an operational threshold current. A ferrite core may be used to increase the inductance of the coil, however a coil winding machine must then be used which increases cost. The coil antenna may also increase the size of the RFID tag. The rate of data transfer from a low radio frequency tag is constrained by the low radio frequency.

In the context of this specification, an animal may be generally any suitable non-human animal or human, including a laboratory animal, a rodent, a rat, a mouse, a cat, a dog, a rabbit, a bird including a poultry bird, livestock including cattle, sheep and horses, or generally any type of animal.

SUMMARY

Disclosed herein is a radio device for implantation in an animal. The radio device comprises a capsule encapsulating at least one of a radio receiver and a radio transmitter.

An embodiment comprises a radio-frequency identification (RFID) device encapsulated by the capsule. The radio-frequency identification device may be responsive to an interrogating radio wave in the ultra-high frequency (UHF) band. The radio device may be a RFID tag wherein the RFID device comprises the radio receiver and the radio transmitter.

An embodiment comprises an antenna encapsulated by the capsule. The antenna may be in signal communication with the RFID device. The antenna may be more than 5 µm and less than 45 µm interior to an outer surface of the capsule. The antenna may be more than 10 µm and less than 20 µm interior to the outer surface. Alternatively or additionally, an embodiment comprises an antenna for the radio-frequency identification device, the antenna having a surface not surrounded by an outer surface of the capsule. The antenna may be at least one of on and at the outer surface. The antenna may be printed on the outer surface.

In an embodiment, the antenna comprises at least one of a monopole antenna, an inverted F antenna, a line dipole antenna, a meander antenna, a fractal antenna and a line antenna.

In an embodiment, the outer surface may comprise a biologically inert ("bio-inert") outer surface.

An embodiment may be configured to be electrically coupled with the animal when implanted therein for receiving an electrical current from the animal. The electric current may be generated by irradiating the animal with a radio wave, for example a RFID device interrogation radio wave.

In an embodiment, the capsule may comprise a tunneling tool for tunneling into the animal. The capsule may comprise a tunneling tool for tunneling into the animal's skin. The tunneling tool may narrow towards an end thereof. The tunneling tool may be at an end of the capsule. The tunneling tool may comprise at least one of a wedge and a point.

In an embodiment, the capsule may be no more than 4.2 mm long. The capsule may be no more than 4 mm long. The capsule may have a maximum transverse dimension of less than 500 μm. The capsule may have a height of no more than 0.2 mm.

Disclosed herein is a method for making a radio device for implantation in an animal. The method comprises the step of encapsulating at least one of a radio receiver and a radio transmitter in a capsule.

An embodiment comprises the step of encapsulating in the capsule a RFID device. The step of encapsulating in the capsule the radio-frequency identification device may comprise encapsulating in the capsule a radio-frequency identification device that is responsive to an interrogating radio wave in the ultra-high frequency (UHF) band.

In an embodiment, the step of encapsulating at least one of a radio receiver and a radio transmitter in the capsule comprises the step of encapsulation an antenna in the capsule. The antenna may be in signal communication with the at least one of the radio receiver and the radio transmitter. The antenna may be more than 5 μm and less than 45 μm interior to an outer surface of the capsule. The antenna may be more than 10 μm and less than 20 μm interior to the outer surface. The antenna may comprise at least one of a monopole antenna, an inverted F antenna, a line dipole antenna, a meander antenna, a fractal antenna and a line antenna.

In an embodiment, the outer surface comprises a biologically inert outer surface.

An embodiment comprises the step of attaching to the capsule an antenna for at least one of the radio receiver and the radio transmitter. The antenna may have a surface not surrounded by an outer surface of the capsule.

In an embodiment, the step of attaching to the capsule the antenna comprises the step of printing the antenna on the outer surface. The antenna may comprise at least one of a monopole antenna, an inverted F antenna, a line dipole antenna, a meander antenna, a fractal antenna and a line antenna.

In an embodiment, the capsule comprises a biologically inert outer surface.

An embodiment comprises the step of configuring the at least one of the radio receiver and the radio transmitter for receiving an electrical current from the animal. The electrical current may be generated by irradiating the animal with a radio wave, for example a RFID device interrogation radio wave.

In an embodiment, the capsule comprises a tunneling tool for tunneling into the animal. The tunneling tool may be for tunneling into the animal's skin. The tunneling tool may narrow towards an end thereof. The tunneling tool may be at an end of the capsule. The tunneling tool may comprise at least one of a wedge and a point.

Disclosed herein is a method for providing electrical power to a radio device attached to an animal. The method comprises the step of electrically coupling the radio device to the animal. The method comprises the step of irradiating the animal with an electromagnetic wave to generate an electric current within the animal, whereby the electric current is conducted from the animal to the radio device.

In an embodiment, the radio device comprises a radio-frequency identification (RFID) device. The radio device may comprise a capsule encapsulating the RFID device.

An embodiment comprises the step of implanting the radio device in the animal. The radio device may be implanted in the animal's tail. The radio device may be implanted in the animal's tail skin.

The animal or a part thereof, for example the animal's tail, may collect and communicate to the radio device an interrogation radio wave. The tail in cooperation with the radio device may broadcast an identification radio wave comprising animal identification information in response to the interrogation radio wave. The tail of the animal may generally act as an antenna itself.

In an embodiment, the step of electrically coupling the radio device implanted in the animal thereto comprises the step of electrically capacitive coupling the radio device implanted in the animal thereto. Alternatively or additionally, the step of electrically coupling the radio device implanted in the animal thereto comprises the step of electrically directly coupling the radio device implanted in the animal thereto.

Collecting electrical current generated in the tail may enable the use of smaller radio devices, and may reduce the need for an antenna to be integral to the radio device. This may reduce animal distress and pain during implantation of the radio device, may enable implantation into parts of the animal previously not suitable for receiving a radio device, and may provide more power to the radio device which may increase the interrogation range, and/or enable additional functionality and applications that require more power.

The antenna, when implanted in the skin, may operate at frequencies at which other antennas not in the animal's skin may not be operable, in view of the reduced attenuation of transmitted and received radio waves. The animal's tail epidermis may be thinner than another part of the animal's epidermis. For example, the thickness of the mouse's tail epidermis may be approximately 30 μm. Electromagnetic waves (for example electromagnetic waves that are transmitted or received by the radio device) that have propagated through the mouse tail's epidermis may be less attenuated than those that have passed through the full thickness of the skin. UHF waves are absorbed relatively strongly by skin tissue.

The radio device, implanted in the animal's tail may migrate less (or not at all) than a radio device disposed within another part of the animal. Handling of the animal for locating a migrated radio device may be reduced or unnecessary.

A radio device and/or antenna within the animal's tail may improve internal imaging of the animal's body. For example, distortion of MRI torso, head, and leg images (by metal within the radio device or a antenna, for example) may be reduced or eliminated.

Disclosed herein is a method for implanting a radio device into an animal. The method comprises the step of making an opening in the skin of the animal. The method comprises the step of inserting the radio device through the opening.

An embodiment comprises the step of inserting an end of a cannula into the opening in the skin. The method comprises the step of the radio device exiting the cannula and entering the animal via the opening.

An embodiment comprises the step of attaching an antenna to the animal. The step of attaching the antenna to the animal's skin may comprise attaching the antenna to the animal for electrically coupling the antenna to the radio device. The step of attaching the antenna to the animal's skin may be such that the antenna and the radio device are co-located. The step of attaching an antenna to the animal comprises the step of applying an electrically conductive tattoo to the animal's skin In an embodiment, the opening in the skin is an incision. Alternatively, the opening in the skin is a piercing.

Disclosed herein is an animal having implanted therein a radio device in accordance with the disclosure above.

In an embodiment, the radio device is within the animal's tail. The radio device may be proximally disposed within the animal's tail. The radio device may be within the animal's skin.

The radio device may be within the animal's dermis. The radio device may be electrically coupled with an external antenna attached to the animal's skin. The external antenna may comprise an electrically conductive tattoo within the animal's skin. The radio device may be co-located with the electrically conductive tattoo. The electrically conductive tattoo may be configured to define at least one externally visible symbol. The at least one externally visible symbol may be human readable. The at least one externally visible symbol may be machine readable. The electrically conductive tattoo may be within the animal's dermis. The electrically conductive tattoo may be within an outer portion of the animal's dermis. The electrically conductive tattoo may be located between 50 µm to 100 µm beneath the surface of the animal's skin. The electrically conductive tattoo may be configured as one of a monopole antenna, an inverted F antenna, a line dipole antenna, a meander antenna, a fractal antenna and a line antenna.

Tattooing the antenna may be easier and/or cheaper than fabricating an RFID tag with an attached antenna. A tattooed antenna may be longer than an antenna that is integral with the radio device, and may improve the performance of the radio device. Generally, animal welfare issues arising from the implantation procedures related to larger RFID tags limit the length of an integrated antenna. A tattooed antenna may enable smaller radio devices to be implanted, improving animal welfare.

The at least one externally visible symbol may be for any one or more or of visual identification of the animal, identifying a feature of the animal including but not limited to the animal's sex, and conveying generally any information. The electrically conductive tattoo may be configured as a meander antenna defining the at least one externally visible symbol. The at least one externally visible symbol may comprise at least one alphanumeric character.

In an embodiment, the animal is a non-human animal. The animal may be any one of a laboratory animal, a rodent, a rat, a mouse, a cat, a dog, a rabbit, a bird including a poultry bird, and livestock.

Disclosed herein is a radio device in accordance with the above disclosure implanted in an animal.

In an embodiment, the radio device is implanted in the animal's tail. The radio device may be implanted at a proximal end of the animal's tail. Alternatively or additionally, the radio device may be implanted in the animal's skin.

In an embodiment, the radio device may be co-located with the electrically conductive tattoo. The electrically conductive tattoo may be configured to define at least one externally visible symbol. The at least one externally visible symbol may be human readable. The at least one externally visible symbol may be machine readable. The electrically conductive tattoo may be within the animal's dermis. The electrically conductive tattoo may be within an outer portion of the animal's dermis. The electrically conductive tattoo may be located between 50 µm to 100 µm beneath the surface of the animal's skin. The electrically conductive tattoo may be configured as one of a monopole antenna, an inverted F antenna, a line dipole antenna, a meander antenna, a fractal antenna and a line antenna.

The at least one externally visible symbol may be for any one or more or of visual identification of the animal, identifying a feature of the animal including but not limited to the animals sex, and conveying generally any information. The electrically conductive tattoo may be configured as a meander antenna defining the at least one externally visible symbol. The at least one externally visible symbol may comprise at least one alphanumeric character.

In an embodiment, the radio device may be electrically coupled with an external antenna attached to the animal's skin. The external antenna may comprise an electrically conductive tattoo within the animal's skin.

Any of the various features of each of the above disclosures, and of the various features of the embodiments described below, can be combined as suitable and desired.

BRIEF DESCRIPTION OF THE FIGURES

Embodiments will now be described by way of example only with reference to the accompanying figures in which:

FIG. 1 shows a longitudinal elevational section view of an embodiment of a radio device.

FIG. 2 shows a detail of FIG. 1.

FIGS. 8-11 shows steps of an embodiment of a method for implanting a radio device into an animal.

FIG. 19 shows a bottom view of yet another embodiment of a radio device comprising an antenna disposed within a cannula.

FIG. 20 shows the radio device of FIG. 19 exiting the cannula with the assistance of pin disposed within the cannula.

DESCRIPTION OF EMBODIMENTS

Figure 3:
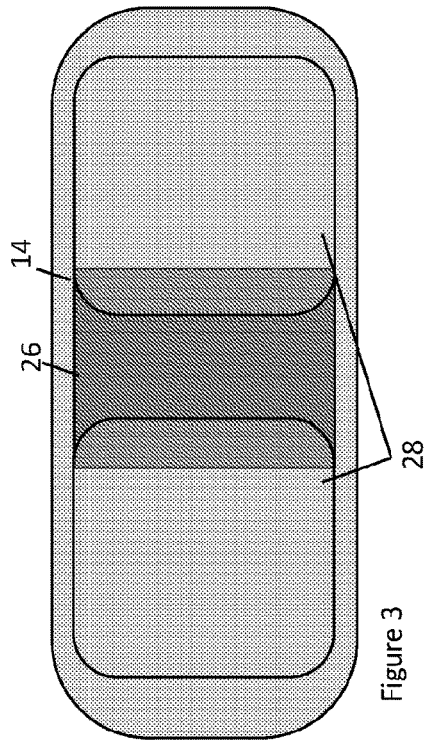
FIG. 3 is a view from above of the radio device of FIG. 1.
Figure 4:
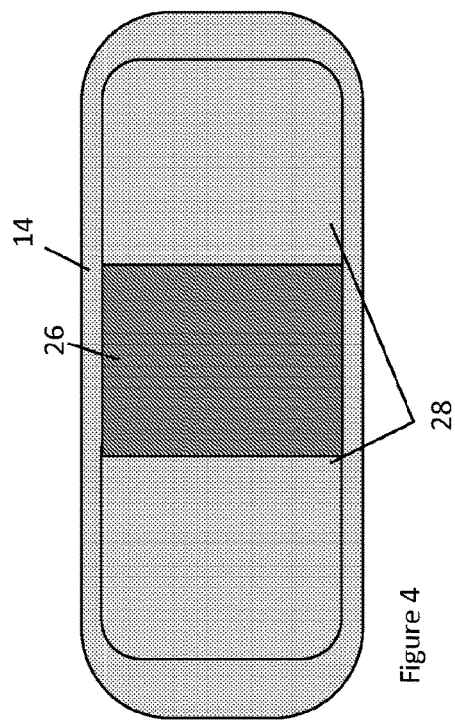
FIG. 4 is a view from below of the radio device of FIG. 1.

FIGS. 1-4 show various views of an embodiment of a radio device, generally indicated by the numeral 10, for implantation in an animal 12. The radio device 10 comprises a capsule 14 encapsulating at least one of a radio receiver 16 and a radio transmitter 18. In this but not all embodiment, the capsule encapsulates both a radio receiver and a radio transmitter.

The animal 12 is a non-human animal 12 in the form of a mouse, however, the animal 12 may be any one of a laboratory animal, a rodent, a rat, a mouse, a cat, a dog, a rabbit, a bird including a poultry bird, and livestock. Alternatively, the animal 12 may be a human.

Figure 5:
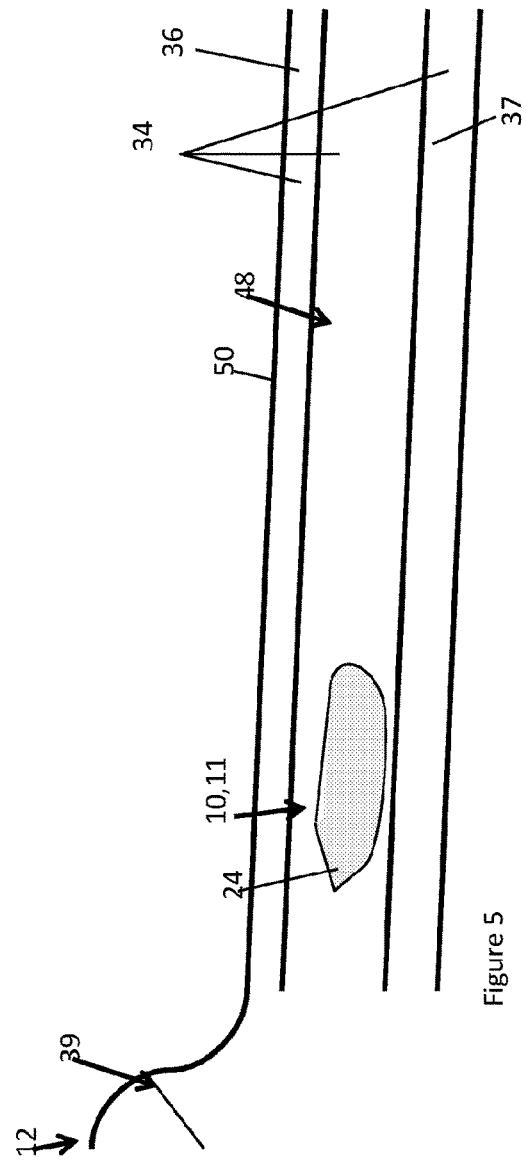
FIG. 5 shows a longitudinal section of a mouse's tail having a radio device of FIG. 1 implanted therein.

FIG. 5 shows an elevational cutaway view of the radio device 10 implanted in the animal 12. The radio device 10 is implanted, in this but not all embodiments, in the skin ("dermis") 34 of the tail 13 of the animal 12, and particularly in an outer portion 48 of the skin 34, beneath the epidermis 36 and above the hyperdermis 37. The tail is beyond the hairline 39 on the animal's torso. The dermis has an approximate thickness in the range of 200-400 μm in some rodents. While in this embodiment the radio device is within the dermis, the radio device may be immediately below the epidermis (specifically, the basal layer thereof) or within the hypodermis. The precise location of the tag implant position will vary according to each tail 13 dimensions—which vary by species, strain, age, litter size gender, etc.

The capsule 14 of the radio device 10, but not in all embodiments, comprises a tunneling tool 21 for tunneling into the animal 12, for example into the animal's skin 34 for implantation therein. The tunneling tool 21 is at an end of the capsule 14, and narrows toward the end 22. The tunneling tool 21 comprises a wedge 24 having a distal edge 27, however it may alternatively comprise, for example, a cone having a point 27, or a tip. Generally, the tunneling tool may have any suitable configuration.

The radio device may be attached to another part of an animal, for example the foot pad of a bird or intrascapularly. Generally, the radio device may be attached to any suitable part of an animal.

Figure 6:
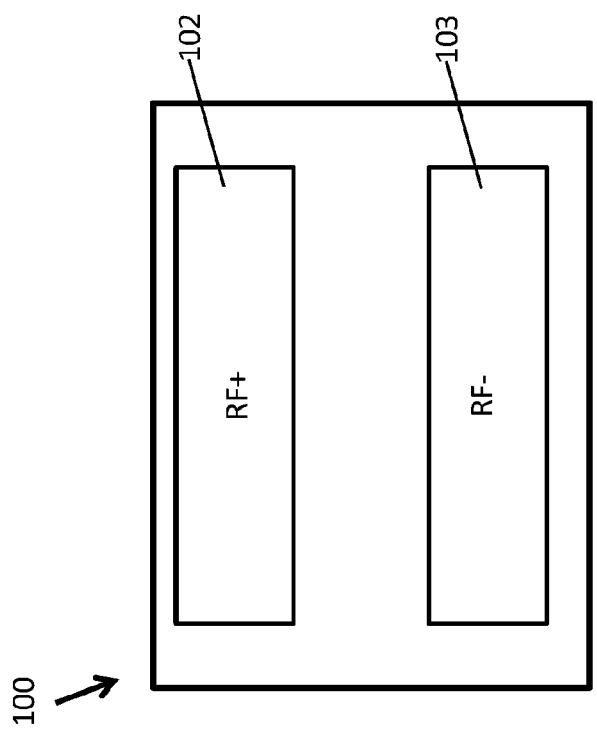
FIG. 6 shows a bottom view of an example of a commercially available RFID semi-conductor microchip.

In the embodiments illustrated, the radio device 10 is in the form of a RFID tag and comprises a radio-frequency identification (RFID) device 26 in the form of a RFID microchip that is encapsulated by the capsule 14. The RFID microchip 26 allows radio identification of the animal. FIG. 6 shows an example of a commercially available RFID semi-conductor microchip 100, the MONZA R6-P manufactured by IMPINJ, that may be integrated with the RFID tag 10. Visible in FIG. 6 are a positive terminal 102 ("RF+") and a negative terminal 103 ("RF−") that are each in the form of an antennae pad for connecting an antenna. The capsule 14 is approximately 450 μm-500 μm high and approximately 4.2 mm long. Other embodiments, however, may have other dimensions, for example may be no more than 4 mm long and have a height of no more than 0.2 mm. The RFID device 26 is 150 μm high and has a top surface area of 464 μm×442 μm. The semi-conductor integrated circuit 100 has read and write capabilities and a memory to store data, operating in the Ultra High Frequency (UHF) band for example, in the range of 860 MHz to 920 MHz to ISO 18000-6 and EPC Gen 2 standards), configured to work within the regulated power maximum of 4 watts EIRP for the USA and other countries that operate to this standard and 2 watts ERP for the European Union.

Applications of the radio device include:
Identification of non-human animals in research laboratories, for example, during preclinical trials.
Identification of domesticated and husbandry animals.
Tracing a non-human animal for human consumption through a process, including identifying and tracking the animal's carcass e.g. poultry, cattle or lamb carcass) after slaughter.

The electromagnetic wave that provides power to the RFID tag 14 is in this but not necessarily in all embodiments a RFID an interrogation radio wave from a RFID reader, for example. The RFID tag 10 responds to receiving the RFID interrogation radio wave, by the RFID device 26 of the RFID tag 14 generating an identification radio signal carrying information in the form of identification information which is transmitted as the identification radio wave. The radio signal 32 is generated according to an air interface protocol which may be any suitable air interface protocol, for example RAIN RFID, and EPC global UHF Class 1 Gen2/ISO 18000-63 (formerly 18000-6C).

The identification information may be unique, or at least unique for a group of animals. However, the identification information may not be unique, but rather identify some other feature of the animal, for example the sex and genetic characteristic. Generally, but not necessarily, the identification information comprises a code in the form of an Electronic Product Code (EPC) is stored in the RFID tag's memory. The code is written to the RFID tag 10 by a RFID reader, and which may take the form of, for example, a 96-bit string of data. Alternative embodiments may not store an EPC. The first eight bits may be a header which identifies the version of the air interface protocol. The next 28 bits may identify the organization that manages the data for this tag. The organization number may be assigned by the EPC global consortium. The EPC or part thereof may be used as a key or index number to uniquely identify that particular animal represented in a data store in the form of an electronic database. In this embodiment, stored in RFID tag user memory is an object class, identifying the kind of animal the tag is attached to (e.g. "mouse" or "rat"), and a unique number for a particular tag encoded as follows:

Position 1=Gender
  0=Male
  1=Female
Positions 2-9
  Enclosure identification (2 numeric digits—00 to 99 which addresses 8 bits, 2-5 for the first digit 0-9 and positions 6-9 for the second digit 0-9)
Positions 10-18
  Strain code (00-9Z)
Positions 19-26
  Protocol identification—a two digit numeric code The radio-frequency identification device 26 is responsive to an interrogating radio wave in the ultra-high frequency (UHF) band.

The radio device 10 comprises an antenna 28 encapsulated by the capsule 14. The antenna is in signal communication with the RFID device 26 when the radio device 10 is implanted. The antenna 28 is electrically coupled with the skin 34 of the tail 13, which may leverage the electrical conductance properties of the skin. The antenna height is approximately 300 μm, the length is approximately 2 mm, and comprises a conductive coil in the form of a coil of 24 gauge round copper wire. The orientation of the antenna relative to the animal may not be important. The antenna 28 may be more than 5 μm and less than 45 μm interior to an outer surface 32 of the capsule 14, however some embodiments may have better performance when the antenna 28 is more than 10 μm and less than 20 μm interior to the outer surface 32. In the embodiment of FIGS. 1-4, the antenna 28 has an outer surface 30 that is 15 μm interior to the outer surface 32. The antenna 28 does not have to be in direct contact with the outer surface 32. The outer surface 32 may protect the animal from harmful materials e.g. copper within a copper antenna and may also protect the antenna from the corrosive environment in the skin.

The antenna 28 is connected to the RFID device 26 using a fusible metal in the form of a fusible metal alloy, for example a solder. Alternatively, conductive epoxy resin a mechanical electrical terminal, for example, may be used. The RFID device 26 is monostatic, however other embodiments may be bistatic (that is, have separate antenna for receiving the interrogation radio wave and transmitting the identification radio wave).

Figure 7:
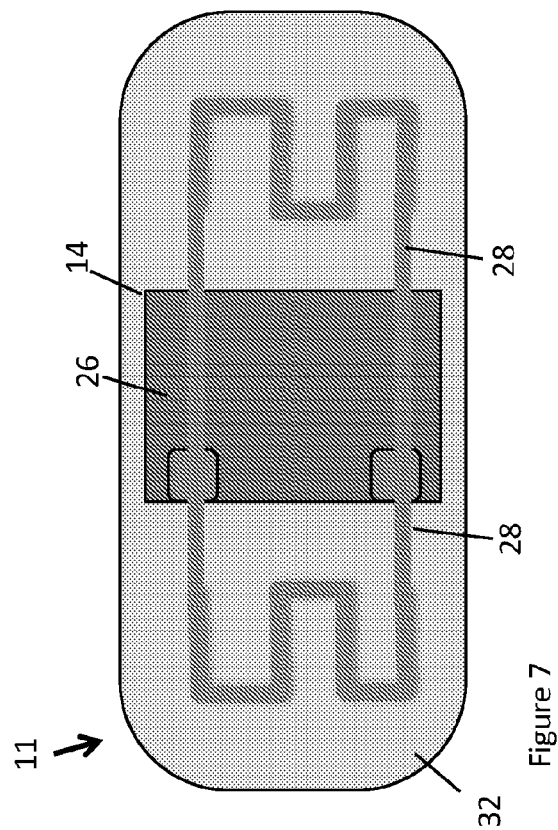
FIG. 7 is a view from below of another embodiment of a radio device comprising an antenna.

An alternative embodiment of a radio device 11 in the form of a RFID tag is shown in FIG. 7. Parts having similar form and/or function to those in FIGS. 1-4 are similarly numbered. The radio device 11 comprises an antenna 28 for the RFID device 26. The antenna 28 is in signal communication with the RFID device 26. The antenna 28 has a surface not surrounded by an outer surface 32 of the capsule 14. The antenna 28 is at least one of at or on the outer surface, and in this embodiment is printed on the outer surface 32. The antenna 28 comprises a loop dipole antenna, with a meander configuration, however it may comprise at least one of a monopole antenna, an inverted F antenna, a line dipole antenna, a meander antenna, a fractal antenna and a line antenna. A fractal antenna is an antenna that uses a fractal, self-similar design to maximize the length, or increase the perimeter (on inside sections or the outer structure), of material that can receive or transmit electromagnetic radiation within a given surface area or volume.

The capsules 14 of FIGS. 1-4 and 7 comprise a biologically inert outer surface 32, comprising for example glass, parylene, polymethylmethacrylate latex (PMMA) or generally any suitable form of biologically inert material. In these embodiments, the capsule comprises a protective biologically inert material in the form of PMMA that encapsulates the RFID device. A biologically inert material may not initiate a response or interact with biological tissue when implanted therein. Materials that initiate a response may detrimentally affect the animal 12. Tissue, however, may still attach to a biologically inert material.

The radio devices 10 and 11 are configured to be electrically coupled with the animal 12 when implanted therein for receiving an electrical current generated by irradiating the animal 12 with a radio wave. The antenna may not be required because the animal's tail 13 may be an antenna. A shorter antenna may be used. The radio device may be read from and written to from a greater distance, for example greater than 3 cm. The antenna may also alternatively or additionally generate electrical power when receiving the electromagnetic wave.

Steps of an embodiment of a method for making either one of the radio devices 10 and 11 for implantation in an animal 12 will now be described. The method comprises the step of encapsulating at least one of a radio receiver 16 and a radio transmitter 18 in a capsule 14. The method may comprise the step of encapsulating an RFID device 26 comprising the radio receiver and radio transmitter.

The RFID device may be one of a plurality of RFID devices attached to a tape reel. The embodiment may include at least one of the steps of:

1. Forming the antenna. The antenna may comprise, for example, 2×2 mm copper wire strips, a dipole loop, a dipole meander loop, etc. A length of copper wire may be coiled or formed by hand or machine to the desired antenna configuration.
2. Removing the RFID device 26 from the tape reel.
3. Attaching the antenna to the RFID device 26, for example to RF+ and RF− pads.
4. Encapsulating the RFID device 26, which may include the steps of, for example:
   Preparing a base layer of encapsulation material
   Positioning the RFID device 26 centrally on the base layer of the encapsulating material
   Covering the RFID device 26 with encapsulating material with, for example, a layered deposition process
   Alternatively or additionally, preparing a base layer of the encapsulating material within a mould, position the RFID device centrally on the base, then injecting the encapsulation material into the mould to encapsulate the RFID device 26.

An embodiment for making of the radio device 10 comprises the step of encapsulation in the capsule 14 an antenna 28.

An embodiment for making a radio device 11 comprises the step of attaching to the capsule 14 an antenna 28 for the radio-frequency identification device 26. The antenna 28 has a surface not surrounded by an outer surface 32 of the capsule 14. The antenna may be disposed on or at the outer surface 32, for example printed on the outer surface 32.

Now a method for providing electrical power to a radio device 10,11 attached to an animal 12 with be described. The method comprises the steps of electrically coupling the radio device 10,11 to the animal 12 thereto. The method comprises the step of irradiating the animal 12 with an electromagnetic wave to generate an electric current within the animal 12, whereby the electric current is conducted from the animal 12 to the radio device 10,11.

The radio device 10,11 is implanted in the skin of the animal's tail 13, however it may be attached to the skin with adhesive, for example. It may be implanted elsewhere in alternative embodiments.

The radio device 10,11 is implanted interior of the animal 12's epidermis 36, which is generally 30-50 μm thick in a mouse.

The tail 13 of a rodent, such as a mouse or rat, generally acts as an antenna or an extension of the antenna attached to the radio device. When the radio antenna 28 is electrically coupled with a rodent tail 13, the received signal strength was found to generally increase. In a trial performed by the applicant, a bare 4 mm copper monopole antenna radiated with an electromagnetic wave having a frequency between 860 MHz and 915 MHz (for example 900 MHz, however radio frequencies outside of this range are expected to be similar affected) generated a signal strength of a relative power of −35 dB. When the bare antenna is increased in length to 8 mm, the signal increased by 4 dB. When a 4 mm copper monopole antenna is inserted into the dermis of a mouse tail 13 of length 18 mm, the signal increased by 8-9 dB can be observed. When the mouse tail length is increased to 26 mm, the signal increased by 10-10.5 dB. When a 4 mm copper monopole antenna is inserted into a fully grown adult mouse tail 13, of 8 months in age, with a length of 98 mm, the signal increased by 14.5 dB. Similar increases in signal may be observed by using rat tails 13. Increasing the effective antenna length using the tail increases received and transmitted signal strength.

The increased electrical power received by the RFID device may support more complex circuitry on a semiconductor chip, or increased interrogation distances.

During the trial, the orientation of the antenna relative to the electromagnetic wave source, whether it is in the tail 13 directly facing the source or in the tail 13 furthest away from the source, behind the tail bone and vasculature, makes no significant difference to the dB gain. Shielding the antenna with a nonconductive material, such as nylon did not attenuate the signal.

While not wanting to be bound to any particular theory, the applicant is of the opinion that it is the electrically conducting properties of the skin of the tail, and the tails longitudinal geometry, that may enable it to act as an antenna.

The step of electrically coupling the radio device 10 implanted in the animal 12 thereto comprises the step of electrically capacitive coupling the radio device 10 implanted in the animal 12 thereto. The radio device 10, for example, has an internal antenna, and so there is no or little direct electrical coupling. Capacitive couple may occur, however. Alternatively, the step of electrically coupling the radio device 11 implanted in the animal 12 thereto comprises the step of electrically directly coupling the radio device 10 implanted in the animal 12 thereto. For example, the antenna 28 on the exterior surface of radio device 11 may be directly coupled with the skin when the device 11 is in implanted in the skin 34.

Now steps of an embodiment of a method for implanting a radio device 10, 11 into an animal 12 will be described with reference to FIGS. 8-11. A step comprises making an opening 38 in the skin 34 of the animal 12 in the form of an incision or hole. Optionally, biologically inert and sterile mineral oil may be applied to the skin surface 50 to lubricate the skin to facilitate the creation of the opening 38 in the skin 34. The skin-piercing or cutting tool may be in the form of, for example, a trocar, or a sharp blade or generally any suitable tool. In another example, the incision may be made using a laser or radio frequency cutting device. As shown in FIG. 9, a step comprises inserting an end of a cannula 40 into the opening 38 in the skin 34. The dermis separates around the leading edge of the cannula as it is inserted therein. As shown in FIG. 10, a step comprises moving the radio device 10,11 through the cannula 40 and out of an opening 41 at the end of the cannula 40. The cannula 40 may then be removed. In the embodiment shown in FIGS. 8-10, a curved cannula 40 with a 20 gauge 0.8 mm lumen is used. The sharp point of the cannula pierces the epidermis and then the cannula is rotated 90° The skin 34 may close around the radio device 10,11 and the opening 38, and the skin may begin to heal.

In this example, the cannula 40 is inserted into the animal's dermis, specifically an upper dermal layer below the epidermis. Alternately, the cannula 40 is inserted between the upper dermal layer and the epidermis. In another embodiment, however, the radio device 10,11 may be implanted at any suitable location within the animal, for example interscapularly.

Figure 12:
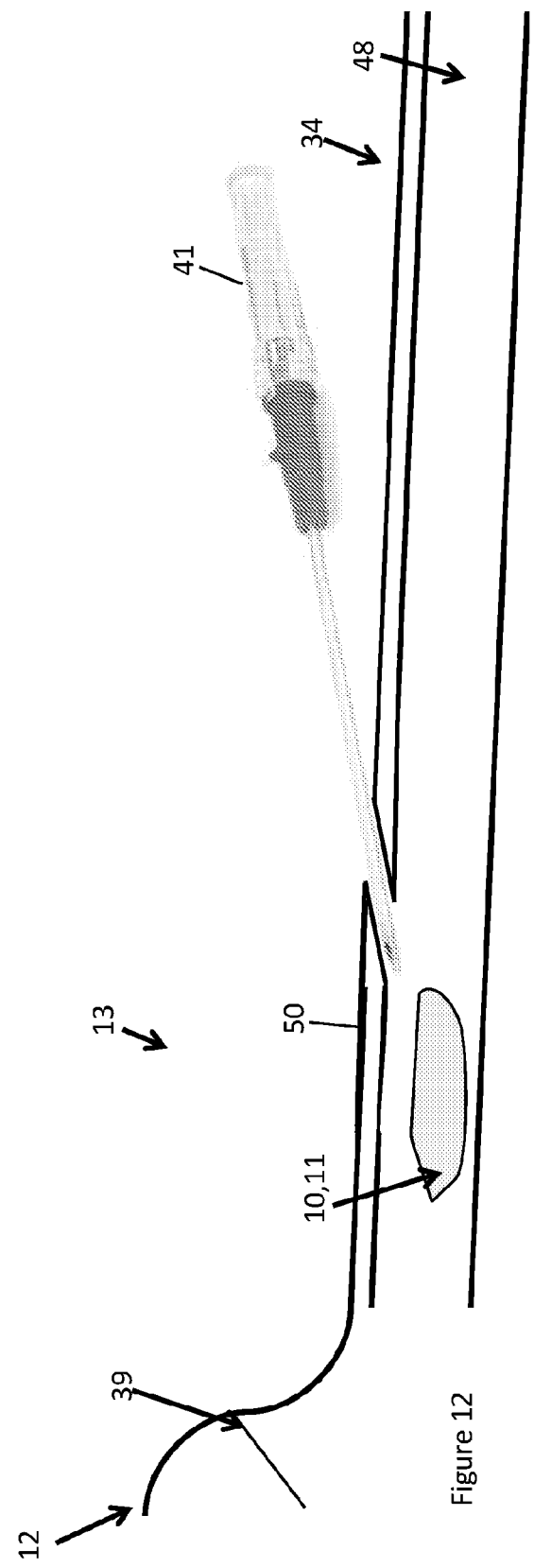
FIG. 12 shows a step of another embodiment of a method for implanting a radio device into an animal.

FIG. 12 shows the implantation of the radio device 10,11 using a straight cannula 41, in which case the sharp point of the cannula pierces the epidermis and is then angled toward the surface of the tail 13, lifting the epidermis above it to provide a straight passage of the device 10,11 to the implantation site.

When the RFID tag 10,11 is pushed into a dermal incision, along for example the epidermal/dermal boundary, the wedge 24 (or point for example), which is the leading edge separates the boundary to form a tunnel without pain or trauma. A gap is left behind the RFID tag 10,11 when it is removed, which may enable the dermal incision to heal unimpeded.

FIG. 19 shows a bottom view of yet another embodiment of a radio device 100 in the form of a RFID tag comprising an antenna disposed within a cannula 102. FIG. 20 shows the radio device 100 of FIG. 19 exiting the cannula 102 with the assistance of a plunger 104 in the form of an actuatable pin, which is disposed within the cannula. The pin 104 is in contact with an end of the radio device 100. The sharp point 108 of the cannula 102 pierces the epidermis and is then angled toward the surface of the tail 13, lifting the epidermis above it to provide a straight passage of the device 100 to the implantation site. The cannula 102 may be pushed into the skin to form a tunnel therein, with the tip 108 separating the skin. The RFID tag may be 100 pushed longitudinally by the plunger 104 disposed in the cannula 102 towards the torso for a distance of 5-6 mm. The RFID tag 100 may be implanted below the basal layer of the epidermis, in the dermis, leaving a 1-2 mm space behind the RFID tag 100 for the opening in the skin to close and the skin to heal. In this embodiment, however, the cannula 100 is pushed 5-6 mm beneath the epidermis and when the cannula 100 is retracted, the plunger 104 is held in place and so retains the position of the RFID tag 100, thus depositing it in the correct place. The plunger 102 in the cannula 104 pushes the RFID tag 100 down and through the lumen 106 to the distal end and out into the dermis below the basal layer. The plunger 104 may push the tag for a distance of 3-4 mm out of the cannula 102, which is then withdrawn. The radio device 100 does not in this case require a tunneling tool. While the action of the plunger and cannula have been described with respect of radio device 100, it will be appreciated that radio device 10 or radio device 11 may be similarly implanted using the plunger 104 and cannula 102. The radio device 100 has a length of 4 mm, width 0.5 mm and a height of 0.2 mm. The radio device comprises an assembly comprising a RFID device 110 in the form of an IMPINJ MONZA RP-6. The assembly has a dipole antenna 112 comprising 2 parts that are each 2 mm long strips of copper that are gold plated. The assembly comprises an antenna substrate in the form of a sheet of KAPTON 114. The assembly is encapsulated in parylene, the encapsulating layer of parylene having a thickness of 2-5 µm.

Steps of an embodiment of a method for making the radio device 100 for implantation in the animal 12 is now described. The steps include at least some of:

Printing the antenna 112 onto a sheet of KAPTON. A plurality of antenna may be printed on the sheet of KAPTON.

Depositing solder in the form of solder paste on the sheet, for example using a screen printing process, for attachment of the antenna to the RFID device. The solder may be deposited between the two antenna, or applied to each antenna well by hand or automatically. This may be repeated if there are a plurality of antennae on the sheet of KAPTON.

An RFID is placed on the solder with the RF pads face down and may be capacitively connected to the antenna. The plurality of RFID device chips may be picked from a wafer with all the dies in place, or the wafer may be packaged with the dies transferred to a waffle or reel tape.

The temperature of the KAPTON sheet is raised such that the solder melts. The temperature of the KAPTON sheet is lowered such that the solder solidifies, whereby the solder fixes the RFID device to the antenna.

Adhesive in the form of DIMAX is placed over each chip and cured with UV light. The cured adhesive provides a smooth surface over the chip edges, which may be sharp because the chip comprises silicon.

The plurality of assemblies may be cut from the sheet of KAPTON using either steel die cuts and/or a laser cutting tool.

An assembly, or each of the plurality of assemblies separated from the sheet of KAPTON, is tumbled in a chamber containing vaporized parylene which coats the tags uniformly over all surfaces.

The completed radio devices may be individually interrogated for testing, for example by an IMPINJ INDY RS2000 reader.

One or more of the radio devices may then be loaded into a cannula or needle, for example, with a 21 or 22-gauge lumen for example, although lumen of other diameters may be used. Using a thin-walled cannula or needle may enable cannulas having smaller diameters to be used. The cannula or needle may be metal, plastic, or generally any suitable material.

Figure 13:
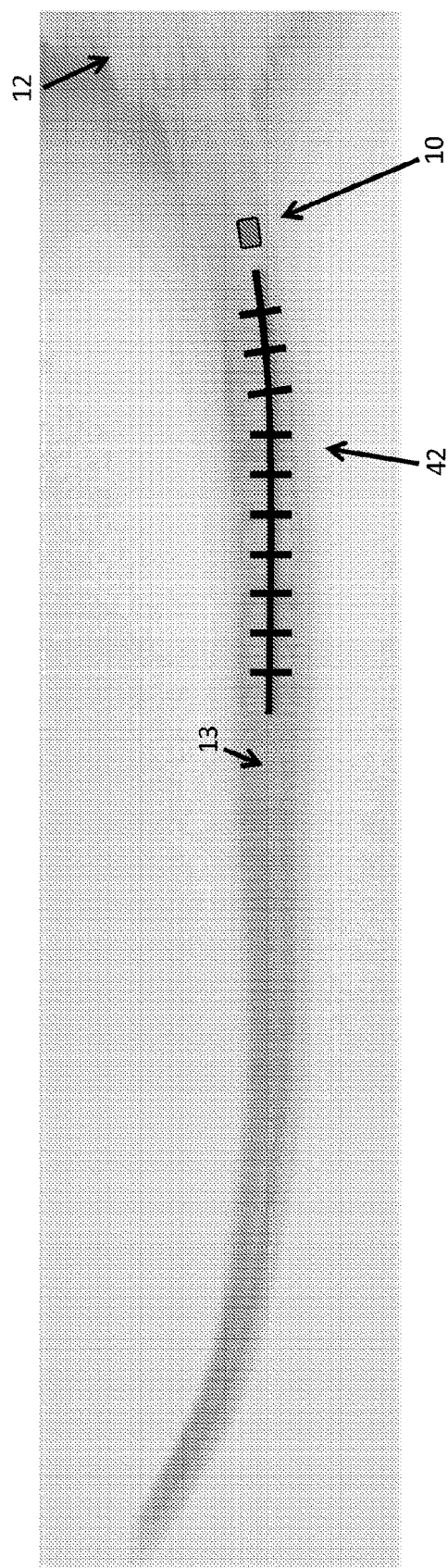
FIG. 13 shows an example of a tail of an animal having implanted therein a radio device of FIG. 1 and an example of an electrically conductive tattoo applied thereto.
Figure 14:
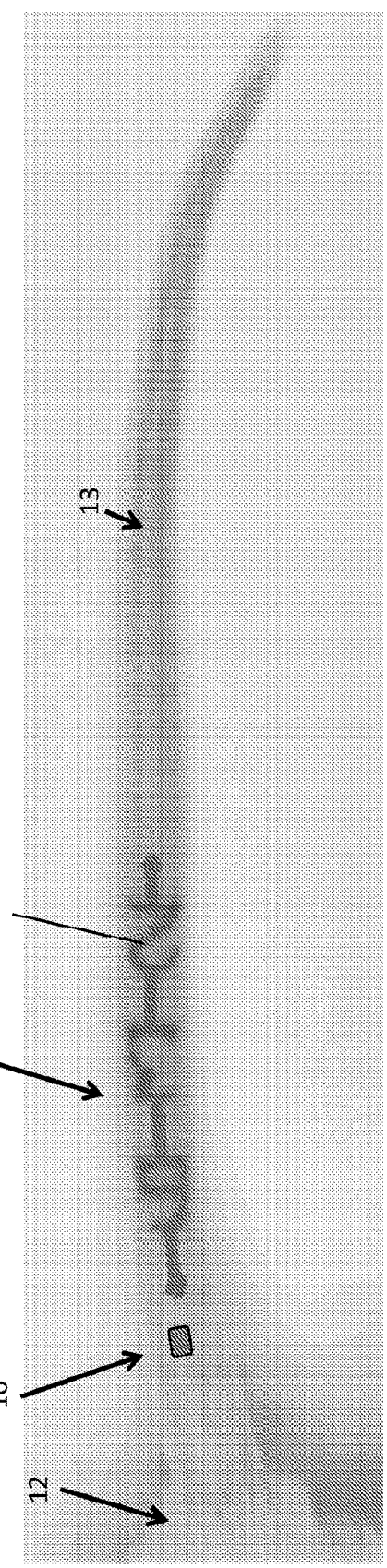
FIG. 14 shows another example of a tail of an animal having implanted therein a radio device of FIG. 1 and another example of an electrically conductive tattoo applied thereto.

As shown in FIGS. 13 and 14, the radio device 10 may be, but not necessarily, electrically coupled with an external antenna 42,44 attached to the animal's skin 34. An embodiment comprises the step of attaching an antenna 42,44 to the animal 12. The step of attaching the antenna 42,44 to the animal 12 comprises, in this but not all embodiments, the step of applying an electrically conductive tattoo to the animal's skin 34. The tattoo 42, 44 is generally but not necessarily disposed in the dermis, for example the upper dermis, to be co-located with the radio device 10. The tattoo material deposit is an unbroken pattern of ink, to form an electrically conductive antenna. The tattoo may comprise a conductive material in the form of a conductive ink or conductive paint, examples of which include but are not limited to copper paint, and reduced graphene oxide ink. Generally, any suitable conductive material may be used, in this embodiment an ink that comprises graphene oxide. The electrically conductive ink is encapsulated to form microspheroids of electrically conductive ink within the dermis. The conductive material may be encapsulated in a polymer, in this embodiment polymethylmethacrylate latex (PMMA), to provide a biologically inert protective coating. The encapsulant may result in fixing the encapsulated conductive material in the dermis. The conductive ink tattooed antenna may be deposited at a mean target depth of 225 μm±50 μm below the surface of the skin 34, however the depth may vary according to the individual, animal variety, species and age. Each microsphere of ink may be, for example, in the range of 1 μm to 10 μm, approximately 5 μm, in diameter. The target thickness of ink deposition may be 75 μm±25 μm. The tattoo antenna length may range between, for example, 15 mm to 40 mm, depending upon the tail length (which varies by species, strain, age, gender and litter size). The tattooed antenna generally may capture more of the electromagnetic wave, and may increase the signal power by between 30 and 50%, for example, depending on its length and the tag antenna length. The antenna may also improve the strength of the radio wave transmitted by the radio device.

The electrically conductive tattoo 42,44 may comprise a monopole antenna, an inverted F antenna, a line dipole antenna, a meander antenna, a fractal antenna and a line antenna, or generally any suitable configuration. The antenna may alternatively be painted onto the animal's skin, or attached with adhesive, however a tattooed antenna is permanent, will not migrate and may be robust.

The antenna length may vary according to the individual tail length. The antenna may be shorter on longer tails, where the tail 13 acts as a longer antenna. The antenna attached to the animal skin 34 may be, for example, approximately 25 mm long.

The devices and methods described in the international patent application publications WO2014/151852A1 and WO/2013/163339 may be used to apply the tattoo. The tattoo material is stored in a reservoir. The tattoo material is pumped to a needle tip which deposits the ink, paint or particulates to a precise depth and location in the dermis as a tattoo.

The electrically conductive tattoo 44 may be configured to define at least one externally visible symbol 46. The at least one symbol may comprise identification information. At least one externally visible symbol is in this embodiment configured to be human readable. Alternatively or additionally, the at least one externally visible symbol may be for machine readability.

The external antenna may alternatively or additionally comprise a monolithic antenna coated in a biologically inert material, for example glass, parylene, polymethylmethacrylate latex (PMMA) or generally any suitable form of biologically inert material. The monolithic antenna may be coated in a highly conductive material under the biologically inert material, such as graphene or graphene oxide. The coating may act as the skin of the antenna rather than the underlying copper or silver metal core. Current generally flows near the surface of the antenna material, only a few microns in metal such as copper and perhaps only 10 microns at 990 Mhz. Therefore, coating the antenna in a material that has higher conductivity than copper or silver, creates a skin for the antenna in which more current will flow, thus enhancing the conductivity of the antenna. Using the coating as the antenna skin may also enable the gauge of the antenna wire to be smaller without loss of performance to the current flow.

Figure 15:
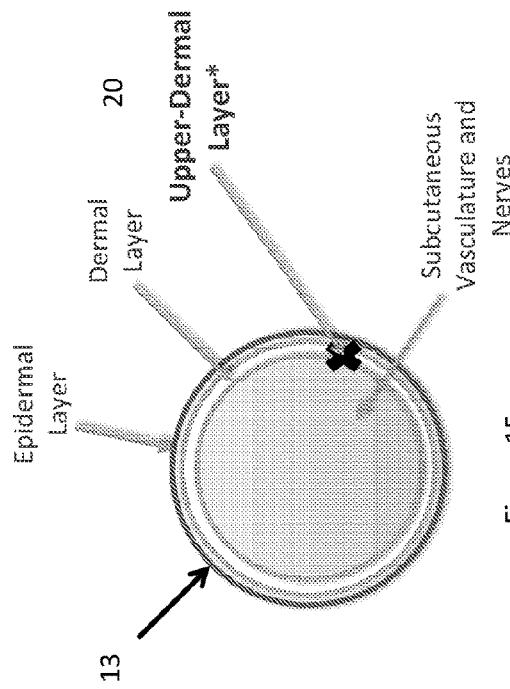
FIG. 15 shows an idealised cross section through the tail of FIGS. 13 and 1614.
Figure 17:
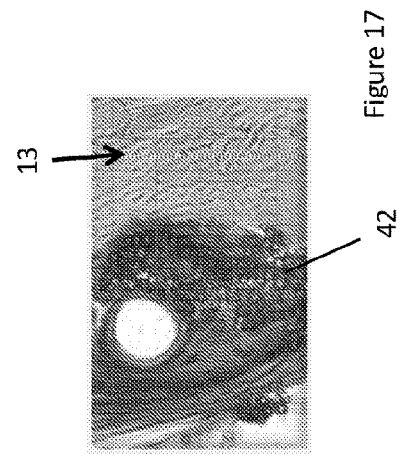
FIGS. 16 and 17 show cross sections through the tail of either FIG. 14 or FIG. 15 captured using a microscope.
Figure 16:
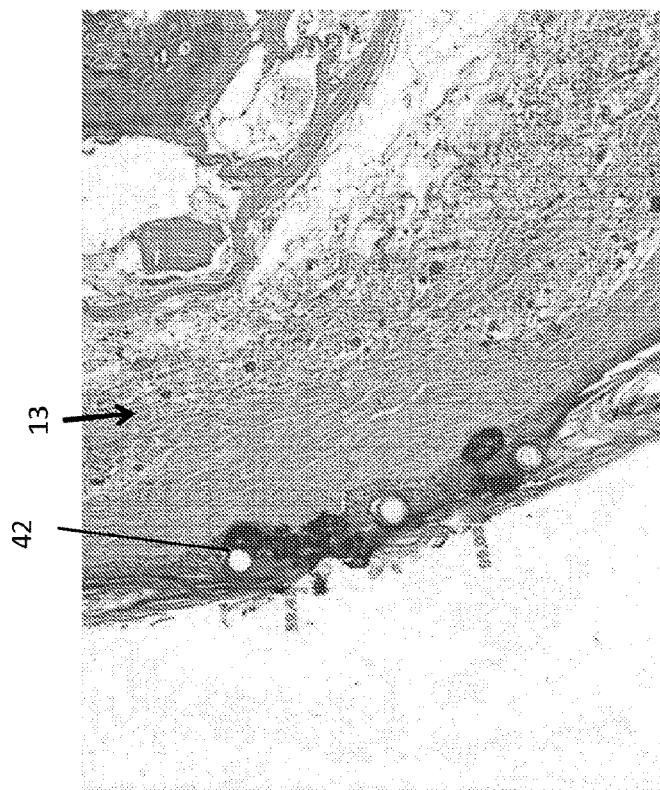

FIG. 15 shows an idealised cross section through the tail 13, and FIGS. 16 and 17 show cross sections of the tail 13 captured using a microscope, revealing the microspheres of the tattoo 42,22.

Figure 18:
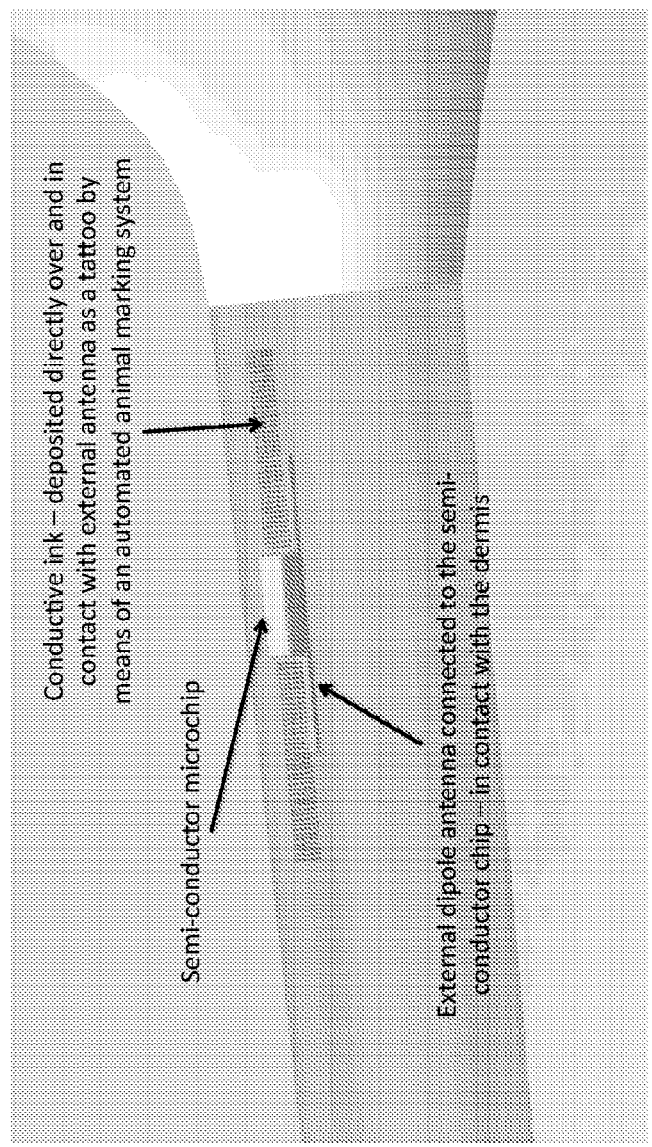
FIG. 18 shows an example of an animal's tail having implanted therein another embodiment of a radio device

FIG. 18 shows an example of an animal's tail having implanted therein another embodiment of a radio device 200 in the form of a semi-conductor microchip. Implanted in the animal is an external antenna electrically coupled to the semi-conductor microchip. An electrically conductive tattoo antenna is in the skin directly over and in contact with the external antenna.

In an alternative embodiment, the RFID tag 14 may comprise a Surface Acoustic Wave (SAW) tag operating at the 2.45 GHz ISM band (to ISO 18000-4 standard). The SAW may require low-level radio frequency (RF) interrogation radio wave pulses of about 10 mW. The SAW tag may be encapsulated in a biologically inert material. The SAW tag may have dimensions of no more than 4 mm in length× 0.8 mm in width and 0.6 mm thick. The SAW tag may be connected to an antenna via its connector pads. An external antenna may be either composed of or coated in a biologically inert highly electrically conductive material. The antenna may be coated in a biologically inert material that does not impede electrical conductance. The SAW tag may provide a minimum 64-bit unique identity code. The SAW tag may be configured to generate temperature data and transmit the temperature data. The SAW may measure another biological parameter, examples of which include but are not limited to the presence of antibodies or electrolyte concentration.

In one example, a RFID tag in accordance with the above disclosure is injected into the dermis of one of the foot pads of a bird, such as a chicken, turkey, duck, goose, grouse, partridge and other edible birds. When slaughtered, at least one of the date, time, location and processing plant identification information may be written to the RFID's microchip memory. When the poultry are received by the processing plant, they use a RFID reader to extract data from the tag and upload the data to a processor in the form of a computing system, to confirm the source of the poultry and other information on the tag to ensure they have the correct shipment for processing. The processor may be configured to alert the end user if the poultry source and details did not match a given manifest.

The position of the implanted RFID tags may vary for various animals that have been slaughtered for processing, such as, but not limited to, cattle, sheep and pigs, and used to track and verify the source of meat when carcasses arrive at processing plants.

An example of a RFID reader is now provided. The RFID reader comprises a host logic device and at least one RFID reader chip in the form of an IMPINJ INDY RS2000 reader chip or generally any suitable form of reader chip. The host is in communication with the reader chip via a UART serial interface or generally any suitable interface. The host comprises a RASBERRY PI, however any suitable host may be used, including QUALCOMM Dragonboard 410c, system-on-a-board and microcontrollers, an example of which is the MSP430 IRI-LT host microcontroller. The reader comprises a printed circuit board assembly (PCBA) comprising the host logic device, RFID reader chip, and firmware. Traces on the PCB electrically connect the host and the RFID reader chip. A user interface for the reader may be presented on a smart phone or tablet computer, for example. The identification information is extracted from the identification radio wave transmitted by the radio device 10,11 and received by the reader and sent via a network to a processor in the form of a computing system, for example a general purpose computer, tablet computer, smart phone, or virtual computer service. The reader may send at least one datagram for communicating at least the animal information (and may include other information from the code) via a packet switched network or inter network that comprises a plurality of networks. Any suitable network may be used, examples of which include but are not limited to a personal area network (e.g. a Universal Serial Bus network, a BLUETOOTH network, a FIREWIRE network, a THINDERBOLT network), packet-switched networks, a local area network (e.g. an Ethernet network defined by the standard IEEE 802.3 or a variant thereof, a Wi-Fi network defined by the standard IEEE 802.11 or a variant thereof, a Fibre Channel network), a metropolitan area network, a wide area network (e.g. packet over SONET/SDH, MPLS, Frame Relay), DUST or another meshed radio network, for example, a ZIGBEE network.

In one embodiment, the RFID reader can be connected to a processor in the form of a tablet or mobile phone, to form a single composite device.

Now that embodiments have been described, it will be appreciated that some embodiments have some of the following advantages:

Embodiments may cause less adverse impact on an animal's health and welfare.
Operators may have reduced skill requirements to perform the implantation procedure.
The implantation procedure may be easier, faster, and/or cheaper with reduced animal stress.
The RFID tag may be reliably read from greater distances (e.g. greater than 3 cm).
Electrically coupling the antenna to the skin may enhance the electrical current to the antenna and radio device, which may improve RFID interrogation range and allow high power consumption applications.
The antenna may be made relatively small when coupled to the skin.
Handling of the animal may be reduced.
There may be less migration of the radio device, especially when implanted in a tail, and subsequently less handling, less adverse physiological reactions, and less fatalities.
There may be less attenuation of received electromagnetic waves, improving signal strength, available power, and the opening up of new operational frequencies.
Animals may be identified visually by humans and machines.
Imaging of the animal's body may be improved.
Animals may be automatically identified with reduced error.

Variations and/or modifications may be made to the embodiments described without departing from the spirit or ambit of the invention. For example, while the RFID has been shown implanted in the tail skin, the RFID may alternatively be implanted in the ear or other area with less hair to interfere with electromagnetic waves, and subcutaneously. The present embodiments are, therefore, to be considered in all respects as illustrative and not restrictive. Reference to a feature disclosed herein does not mean that all embodiments must include the feature.

Prior art, if any, described herein is not to be taken as an admission that the prior art forms part of the common general knowledge in any jurisdiction.

In the claims which follow and in the preceding description of the invention, except where the context requires otherwise due to express language or necessary implication, the word "comprise" or variations such as "comprises" or "comprising" is used in an inclusive sense, that is to specify the presence of the stated features but not to preclude the presence or addition of further features in various embodiments of the invention.

The invention claimed is:

1. A radio device for implantation in an animal, the radio device comprising:
   a radio-frequency identification (RFID) device that is responsive to an interrogating radio wave in the ultra-high frequency (UHF) band received by a dipole antenna,
   wherein the RFID device and the dipole antenna are electrically connected and attached to an antenna substrate, and
   wherein the RFID device, the dipole antenna and the antenna substrate are encapsulated by a coating to form an encapsulated device having a maximum width of less than 1 mm and a maximum height of less than 0.5 mm that is configured to be implanted in a tail of a rodent beyond a hairline of a torso of the rodent using a needle having a diameter of 20-22 AWG.

2. The radio device defined by claim 1 wherein the antenna substrate is a flexible polymide film and the coating is parylene.

3. The radio device defined by claim 1 wherein the encapsulated assembly is no more than 4.2 mm long.

4. The radio device defined by claim 1 wherein the dipole antenna is more than 5 μm and less than 45 μm interior to an outer surface of the encapsulated assembly.

5. The radio device defined by claim 1 wherein the dipole antenna is printed on the antenna substrate.

6. An improved radio device suitable in size and material for implantation in a rodent using a cannula, the radio device comprising a radio-frequency identification RFID device, an antenna in signal communication with the RFID device, and an antenna substrate, wherein the improvement comprises:

the RFID device is configured to be responsive to an interrogating radio wave in the ultra-high frequency UHF band and the antenna is a dipole antenna that receives the UHF band interrogating radio wave; and the radio device is encapsulated by a biologically inert coating to form an encapsulated assembly that has a maximum transverse dimension of less than 500 µm and is configured to be implanted under the skin in a tail of the rodent beyond a hairline of a torso of the rodent using a cannula having an inner diameter of a lumen in the range from 0.6 mm to 0.41 mm.

7. The improved radio device of claim 6, wherein the antenna substrate is a flexible polymide film and the coating is parylene.

8. The improved radio device of claim 6, wherein the encapsulated assembly is no more than 4.2 mm long.

9. The improved radio device of claim 6, wherein the dipole antenna is more than 5 µm and less than 45 µm interior to an outer surface of the encapsulated assembly.

10. The improved radio device of claim 6, wherein the dipole antenna is printed on the antenna substrate.

* * * * *